(12) United States Patent
Rudser et al.

(10) Patent No.: US 10,376,624 B2
(45) Date of Patent: Aug. 13, 2019

(54) TRANSCUTANEOUS ENERGY TRANSFER SYSTEMS

(71) Applicant: HeartWare, Inc., Miami Lakes, FL (US)

(72) Inventors: John Rudser, Miami, FL (US); Stefan Schwarzbach, Wessling (DE)

(73) Assignee: HeartWare, Inc., Miami Lakes, FL (US)

( * ) Notice: Subject to any disclaimer, the term of this patent is extended or adjusted under 35 U.S.C. 154(b) by 611 days.

(21) Appl. No.: 14/686,245

(22) Filed: Apr. 14, 2015

(65) Prior Publication Data

US 2015/0290379 A1    Oct. 15, 2015

Related U.S. Application Data

(60) Provisional application No. 61/979,835, filed on Apr. 15, 2014.

(51) Int. Cl.

| | |
|---|---|
| *A61N 1/362* | (2006.01) |
| *A61M 1/12* | (2006.01) |
| *A61N 1/378* | (2006.01) |
| *A61N 1/372* | (2006.01) |
| *H01F 38/14* | (2006.01) |
| *A61M 1/10* | (2006.01) |
| *H02J 50/10* | (2016.01) |

(52) U.S. Cl.
CPC ............ *A61M 1/127* (2013.01); *A61N 1/3787* (2013.01); *A61N 1/37229* (2013.01); *H01F 38/14* (2013.01); *A61M 1/1086* (2013.01); *A61M 1/12* (2013.01); *A61M 2205/8243* (2013.01); *H02J 50/10* (2016.02)

(58) Field of Classification Search
CPC ...... A61M 1/12; A61M 1/127; A61M 1/1086; A61N 1/37229; A61N 1/3787; H01F 38/14; H02J 50/10

See application file for complete search history.

(56) References Cited

U.S. PATENT DOCUMENTS

| | | | |
|---|---|---|---|
| 5,279,292 | A | 1/1994 | Baumann et al. |
| 5,314,453 | A | 5/1994 | Jeutter |
| 5,690,693 | A | 11/1997 | Wang et al. |

(Continued)

FOREIGN PATENT DOCUMENTS

| | | |
|---|---|---|
| EP | 1166820 A2 | 1/2002 |
| WO | 0197908 A2 | 12/2001 |

(Continued)

OTHER PUBLICATIONS

International Search Report for Application No. PCT/US15/025748 dated Jun. 3, 2016.

(Continued)

*Primary Examiner* — Mallika D Fairchild
(74) *Attorney, Agent, or Firm* — Christopher & Weisberg, P.A.

(57) ABSTRACT

The present disclosure relates to an improved transcutaneous energy transfer (TET) system that generates and wirelessly transmits a sufficient amount of energy to power one or more implanted devices, including a heart pump, while maintaining the system's efficiency, safety, and overall convenience of use. The disclosure further relates one or more methods of operation for the improved system.

2 Claims, 8 Drawing Sheets

(56) References Cited

U.S. PATENT DOCUMENTS

| | | |
|---|---|---|
| 6,324,430 B1 | 11/2001 | Zarinetchi et al. |
| 6,389,318 B1 | 5/2002 | Zarinetchi et al. |
| 7,317,947 B2 | 1/2008 | Wahlstrand et al. |
| 7,945,334 B2 | 5/2011 | Jimenez et al. |
| 8,265,771 B2 | 9/2012 | Donofrio et al. |
| 8,362,742 B2 | 1/2013 | Kallmyer |
| 8,457,758 B2 | 6/2013 | Olson et al. |
| 8,489,200 B2 | 7/2013 | Zarinetchi et al. |
| 8,628,460 B2 | 1/2014 | Yomtov et al. |
| 2003/0171792 A1 | 9/2003 | Zarinetchi et al. |
| 2005/0113889 A1 | 5/2005 | Jimenez et al. |
| 2006/0016452 A1 | 1/2006 | Goetz et al. |
| 2008/0051854 A1 | 2/2008 | Bulkes et al. |
| 2011/0071597 A1 | 3/2011 | Aghassian |
| 2011/0257703 A1 | 10/2011 | Kerber et al. |
| 2012/0112552 A1 | 5/2012 | Baarman et al. |
| 2012/0119698 A1 | 5/2012 | Karalis et al. |
| 2012/0146575 A1 | 6/2012 | Armstrong et al. |
| 2013/0093390 A1 | 4/2013 | Partovi |
| 2013/0096652 A1 | 4/2013 | Ozawa et al. |
| 2013/0127253 A1 | 5/2013 | Stark et al. |
| 2013/0158631 A1 | 6/2013 | Shea et al. |
| 2013/0184785 A1* | 7/2013 | Aghassian ........... A61N 1/3787 607/59 |
| 2013/0208390 A1 | 8/2013 | Singh et al. |
| 2013/0208391 A1 | 8/2013 | Lee |
| 2013/0304158 A1 | 11/2013 | Zarinetchi et al. |
| 2013/0310629 A1 | 11/2013 | Lafontaine |
| 2013/0310630 A1 | 11/2013 | Smith et al. |

FOREIGN PATENT DOCUMENTS

| | | |
|---|---|---|
| WO | 2013109605 A1 | 7/2013 |
| WO | 2013164831 A1 | 11/2013 |
| WO | 2014018967 A1 | 1/2014 |
| WO | 2014018968 A2 | 1/2014 |
| WO | 2014059962 A1 | 4/2014 |

OTHER PUBLICATIONS

International Partial Search Report for Application No. PCT/US20151025714 dated Jul. 6, 2015.

International Search Report and Written Opinion for Application No. PCT/US20151025714 dated Sep. 30, 2015.

Extended European Search Report, dated Nov. 3, 2017, for corresponding European Application No. 17173659.8, consisting of 5 pages.

European Search Report for corresponding application No. EP 18 17 0664, dated Jun. 21, 2018, 6 pages.

* cited by examiner

TRANSCUTANEOUS ENERGY TRANSFER SYSTEMS

CROSS-REFERENCE TO RELATED APPLICATIONS

The present application claims the benefit of the filing date of U.S. Provisional Patent Application No. 61/979,835 filed Apr. 15, 2014, the disclosure of which is hereby incorporated herein by reference.

FIELD OF THE TECHNOLOGY

The present invention relates to transcutaneous energy transfer (TET) systems and methods of operation for such systems.

BACKGROUND

Transcutaneous energy transfer (TET) systems are used to supply power to devices such as pumps implanted internally within a human body. A magnetic field generated by a transmitting coil outside the body can transmit power across a cutaneous (skin) barrier to a magnetic receiving coil implanted within the body. The receiving coil can then transfer the received power to the implanted pump or other internal device and to one or more batteries implanted within the body to charge the battery.

Such systems should efficiently generate and wirelessly transmit a sufficient amount of energy to power one or more implanted devices while maintaining the system's efficiency, safety, and overall convenience of use.

With respect to those systems' efficiency, one drawback suffered by present TET systems arises from the nature of the magnetic field generated by the transmitting coil. By its nature, the field extends from the transmitting coil in every direction. As such, much of the energy from the electromagnetic field emitted by the transmitting coil is not focused effectively or optimally at the receiving coil. This limits the efficiency (i.e., the coupling coefficient) of the wireless energy transfer. Another challenge arises from the fact that power and/or current demands of an implanted device are not constant but rather subject to vary. As such, there is a need to efficiently accommodate such changes in power and/or current demand in order to most effectively power the implanted device.

With respect to convenience of the system, one challenge among present TET systems arises from the difficulty in maintaining optimal axial alignment (in proximity to the surface of the patient's skin) and radial alignment (across the surface of the patient's skin) between the transmitting and receiving coils to increase power transfer efficiency and minimize transmitting coil losses that would result in heating. Firstly, a transmitting coil worn on the exterior of the body is subject to shift in position, such as due to movement by the wearer. Moreover, once the transmitting coil is shifted out of place, repositioning the coil, such as determining in which direction to move the coil in order to reestablish alignment, may be difficult without some form of guidance. As such, there is a need for a system that assists the wearer in positioning or repositioning the transmitting coil.

Further, a shift in the position of a transmitting coil worn on the exterior of the body also poses issues with respect to health and safety of the system's wearer. If the coil shifts out of its proper alignment while operating at full power, not only may the coupling coefficient of the power transfer be reduced, but it may cause unwanted overheating to the wearer, and such overheating may be harmful to the skin or surrounding tissue.

BRIEF SUMMARY OF THE INVENTION

One aspect of the present disclosure provides for a transcutaneous energy transfer system, including: an internal component having a power-consuming device and an internal coil electrically connected to the power-consuming device, the internal component being adapted for mounting within the body of an animal; an external coil adapted for mounting outside of the body; a current monitor operative to measure current flow in the external coil and to provide an indication of whether or not the external coil is electromagnetically coupled to the internal coil based on the measured current flow; and a drive circuit operative to apply a power-level alternating potential to the external coil responsive to an indication from the current monitor that the external coil is electromagnetically coupled to the internal coil. The drive circuit may also be operative to apply a test-level alternating potential less than the power-level alternating potential to the external coil when the not applying the power-level alternating potential. The drive circuit may further be operative to cease application of the power-level alternating potential to the external coil in response to an indication from the current monitor that the external coil is not electromagnetically coupled to the internal coil. The drive circuit may yet further be operative to apply the test-level alternating potential intermittently when the drive circuit is not applying the power-level alternating potential. In further examples, the current monitor may be operative to provide information representing a degree of coupling, and the drive circuit may be operative to apply the power-level alternating potential when the degree of coupling exceeds a threshold value.

Another aspect of the present disclosure provides for a transcutaneous energy transfer system including an internal component adapted for mounting within the body of an animal, and an external component adapted for mounting outside of the body. The internal component includes an internal coil, an internal device electrically connected to the internal coil for receipt of power from the internal coil, and a telemetry transmitter operative to send telemetry signals representing one or more parameters relating to operation of the internal component. The external component includes an external coil, a telemetry receiver adapted to receive the telemetry signals from the telemetry transmitter, a current monitor operative to measure current flow in the external coil and to provide an indication of whether or not the external coil is electromagnetically coupled to the internal coil based on the measured current flow, and a drive circuit operative in a normal mode of operation when the telemetry receiver receives the telemetry signals, and in a safe mode of operation when the telemetry receiver does not receive the telemetry signals. The drive circuit may apply more power to the external coil in the normal mode than in the safe mode. In the safe mode, the drive circuit may apply an amount of power to the external coil sufficient to power the internal device and the telemetry transmitter. In some examples, the drive circuit may be configured to operate in the safe mode only when the telemetry receiver does not receive the telemetry signals and the current monitor indicates that the external coil is inductively coupled to the internal coil. Also, in some examples, the external coil, current monitor, and drive circuit may be disposed within a common housing. Yet further, in some examples, the drive circuit may be operative to drive the external coil so as to supply at least about 20 watts of power to the internal device.

Yet another aspect of the disclosure provides for an implanted component of a wireless energy transfer system, including: a secondary coil having a secondary axis and a secondary conductor extending in a spiral around the secondary axis; a secondary shield composed of a magnetizable, electrically insulating material extending transverse to the secondary axis in proximity to the secondary coil and to the rear of the secondary coil; and a power-consuming device electrically connected to the secondary coil. The secondary conductor may have inner and outer ends disposed substantially on a common radial line perpendicular to the secondary axis. The secondary shield may have a round hole extending through it in alignment with the secondary axis. In some examples, the implanted component may further include an implantable coil housing having a biocompatible exterior surface, containing the secondary coil, and having front and rear sides. A front side of the secondary coil may face toward the front side of the coil housing. Additionally, the coil housing may include one or more visually-perceptible indicia differentiating the front and rear sides of the housing.

Yet a further aspect of the disclosure provides for a driver for a wireless energy transfer system, including: an external coil having a primary axis and a primary conductor extending around the primary axis; a drive circuit operative to drive the external coil so that power applied to the external coil will be coupled to the internal coil; and a shield composed of a ferromagnetic or ferrimagnetic material having electrical conductivity less than about $0.3 \times 10^6 \sigma$ and extending transverse to the primary axis, the shield including a plurality of plate-like segments arranged generally edge-to-edge with one another with gaps between edges of mutually adjacent segments. In some examples, the shield may be composed of a ferrite. Also, in some examples, at least some of the gaps may extend substantially radially with respect to the primary axis.

An even further aspect of the disclosure is directed to a driver for a wireless energy transfer system including: a primary coil having a primary axis and a primary conductor extending in a spiral around the primary axis; a drive circuit operative to drive the primary coil; a main shield composed of a magnetizable, electrically insulating material extending transverse to the primary axis in proximity to the primary coil; and a shield wall composed of a magnetizable, electrically insulating material. The shield wall extends around the primary axis and projects from a rear surface of the main shield facing away from the primary coil, so that the shield wall and main shield cooperatively define a generally cup-like structure. At least a portion of the drive circuit may be disposed within the shield wall.

In some examples, the drive circuit may further include one or more capacitors connected in a resonant circuit with the primary coil and one or more power semiconductors connected to the resonant circuit for supplying power to the resonant circuit. The capacitors and power semiconductors may be disposed within the shield wall.

One more aspect of the disclosure provides for a driver for a wireless energy transfer system including: a primary coil having a primary axis and a primary conductor extending in a spiral around the primary axis; a drive circuit operative to drive the primary coil; and a main shield composed of a magnetizable, electrically insulating material extending transverse to the primary axis in proximity to the primary coil. The main shield may have a hole extending through it in alignment with the primary axis. The hole extending through the main shield may be square.

DETAILED DESCRIPTION

Figure 1:
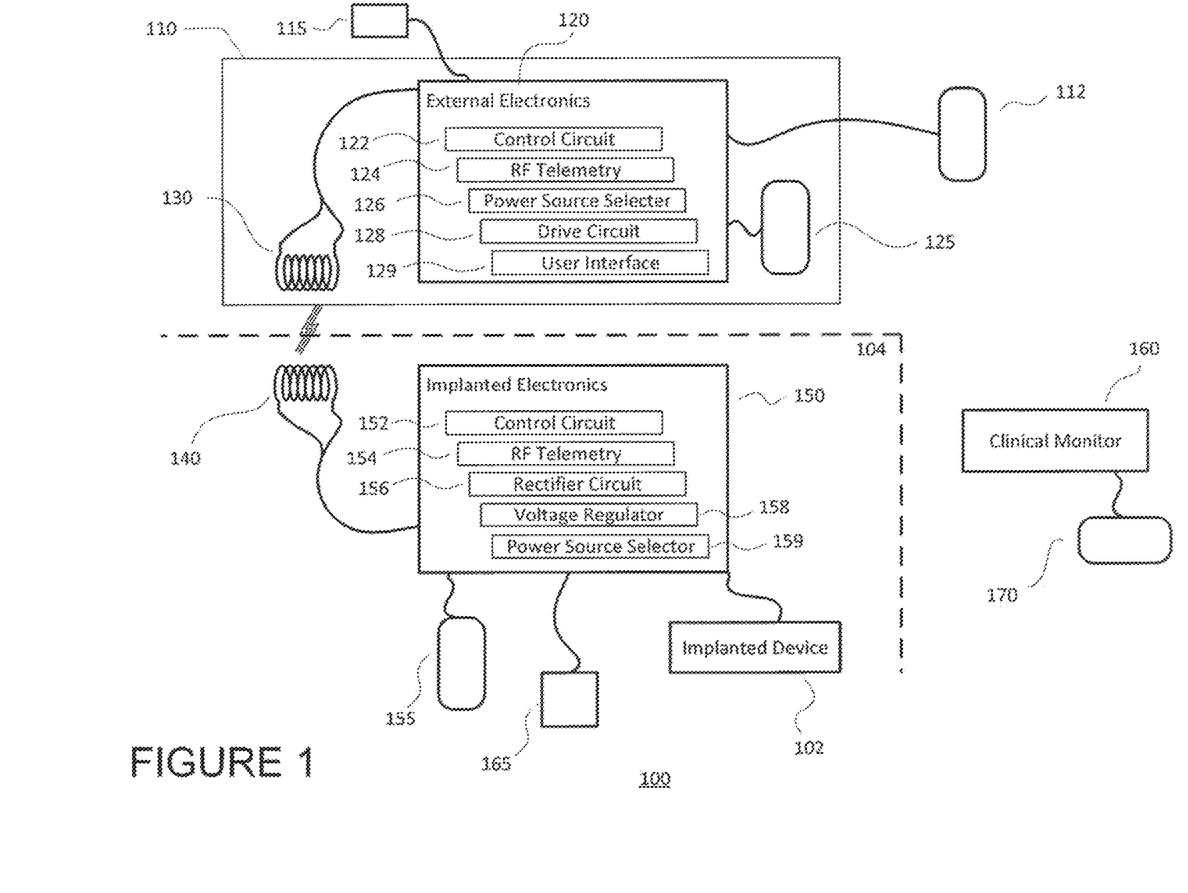
FIG. 1 is a schematic diagram of a transcutaneous energy transfer (TET) system in accordance with an aspect of the disclosure.

FIG. 1 schematically illustrates a transcutaneous energy transfer (TET) system 100 used to supply power to an implanted therapeutic electrical device 102 in an internal cavity within the body, i.e., below the skin of a patient 104. The implanted electrical device 102 can include a pump such as for use in pumping blood as a ventricular assist device ("VAD"), for example. The internal or implanted electrical device 102 can include controlling circuitry to control, for example, a pump.

As illustrated in FIG. 1, the TET system 100 includes both external electronics 120 mounted outside the body of the patient 104, as well as internal or implanted electronics 150 mounted within the body of the patient 104. The external electronics are electrically coupled to one or more power sources, including, for example, an external battery 125 and a building power source 112 (such as AC power, or converted DC power, supplied from an electrical outlet in a building). The external power sources may supply an input voltage anywhere between about 20V and about 250V. The external electronics 120 are also electrically coupled to an external primary coil 130, and the implanted electronics 150 are electrically coupled to an internal or implanted secondary coil 140. The external and implanted coils 130 and 140 are inductively coupled to one another through electromagnetic induction in order to transfer energy wirelessly therebetween. In the example of FIG. 1, the external coil 130 is housed in a common external module 110 together with the external electronics 120, whereas the implanted coil 140 and implanted electronics 150 are not housed together.

The implanted electronics 150 are electrically coupled to an implanted battery 155 and to the implanted electrical device 102. Energy received at the implanted coil 140 is stored in the implanted battery 155, provided to the implanted medical device 102, or both, via the implanted electronics 150. Additionally, energy stored at the implanted battery may be provided to the implanted medical device 102 via the implanted electronics 150.

The external electronics 120 of the system 100 may include control circuitry 122, radio frequency (RF) telemetry circuitry 124, power source selection circuitry 126, drive circuitry 128, and a user interface 129. The power source selection circuitry 126 is configured to select an external power source (e.g., battery 125, wall source 112) from which to provide power to the external coil 130. The drive circuit 128 is configured to drive the external coil 130 such that energy is transferred from the external coil 130 to the implanted coil through electromagnetic induction. The control circuitry 122 is configured to determine and execute instructions for controlling the power source circuitry 126 and drive circuitry 128 in order to control the wireless transfer of energy between the external and implanted coils. Such control may include setting the pulse width and/or frequency of transmission, controlling which power source is selected by the power source circuitry 126, instructing the drive circuitry 128 to drive the external coil 130, etc. Determinations made by the control circuitry 120 may be based on signals received from the telemetry circuitry 124, information received from external sensors 115, and/or inputs from the user interface 129.

The implanted electronics of the system 100 may include implanted control circuitry 152 and RF telemetry 154, as well as a rectifier circuit 156, a voltage regulator circuitry 158, and power source selection circuitry 159. The rectifier circuit 156 may be configured to convert AC power generated at the implanted coil 140 to DC power. The voltage regulator circuit is configured to adjust the voltage level of the converted DC power and power from the implanted battery 155 before being provided to the implanted medical device 102. The implanted power switching circuitry 159 is configured to control whether the implanted medical device 102 is powered from the implanted battery 155, the implanted coil 140, or both. Similar to the purpose of the external control circuitry 122, the implanted control circuitry 152 may be used to determine and execute instructions for controlling the voltage regulation settings of the voltage regulator circuitry 158, power source selections made by the implanted power switching circuitry 159, and overall delivery of power to the implanted medical device 102. In some examples, the implanted control circuitry 152 may further control an efficiency of the inductive coupling between the external and implanted coils 130 and 140, such as by instructing an adjustment in the resonant frequency of resonant circuit components 145 in the implanted coil 140. As with the external circuitry 120, such determinations at the implanted circuitry may be based on RF telemetry 154 signals as well as other information received from internal sensors 165.

The TET system 100 may optionally include a clinical monitor 160 for collecting system parameters (e.g., implanted battery life, charge stored in implanted battery, alarms, etc.) to be monitored, such as by the patient 104 or by a hospital clinical staff. The clinical monitor may include a memory, internal or external, for storing the collected parameters, as well as for logging an event history of the patient 104 (e.g., a low flow condition, a no-flow condition, an interrupt, etc.). The clinical monitor 160 may further be coupled to and receive/transmit information to and from units other than the TET system, such as to and from the patient's watch or smartphone, or to and from a hospital computer database. The clinical monitor 160 may also be powered by its own dedicated power source or battery 170.

In some examples, the clinical monitor 160, aside from receiving and monitoring data from the other components of the TET system 100, may deliver set points or parameters (e.g., a flow rate) pertaining to the desired operation of the system 100. Such set points may be communicated to the external electronics 120, implanted electronics 150, or both as an instruction for operating the system 100, and thereby utilized in setting further parameters of the system's operation, such as a pulse width and/or frequency for driving the wireless energy transmission to power the implanted medical device 102.

Figure 2:
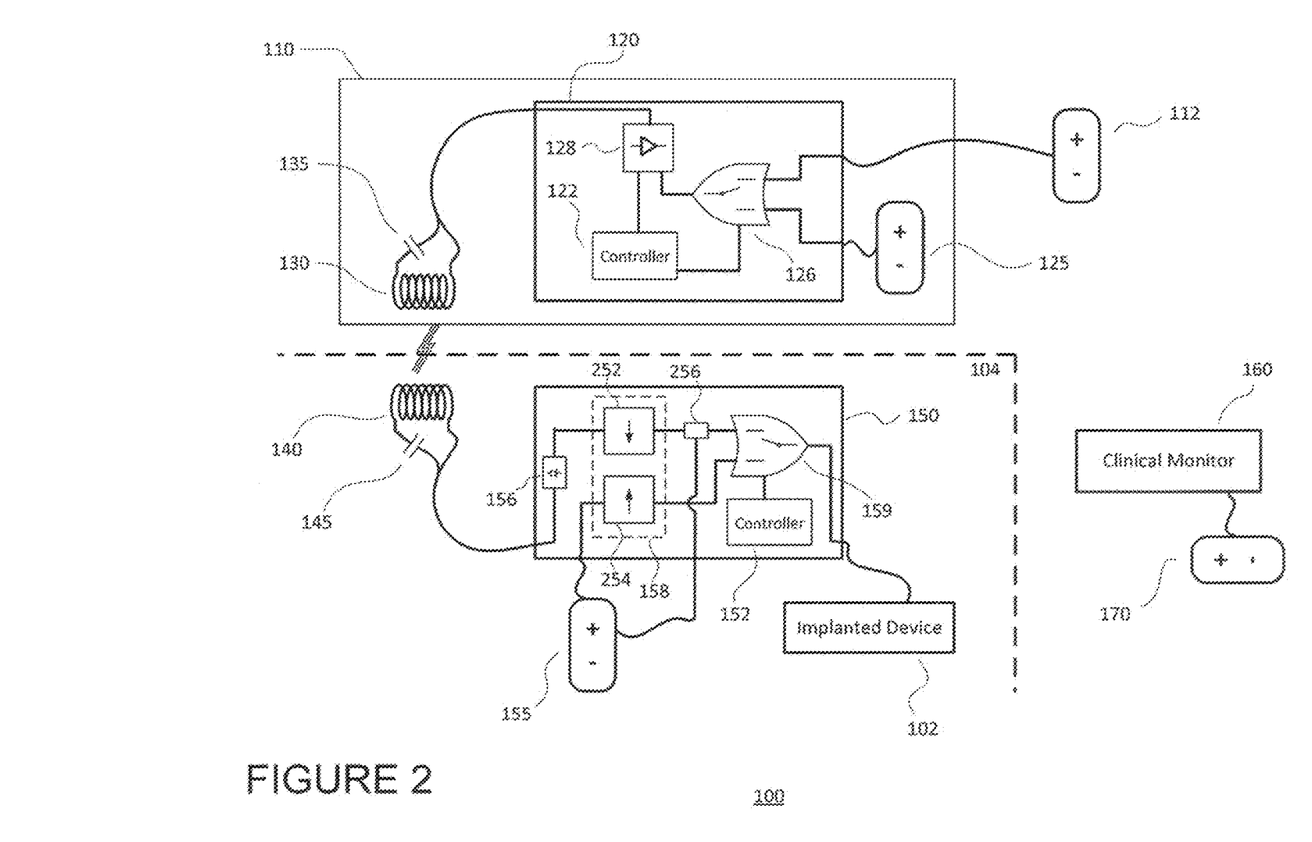
FIG. 2 is a schematic diagram of the power system circuitry for the TET system of FIG. 1 in accordance with an aspect of the disclosure.

FIG. 2 schematically illustrates the power system circuitry of the TET system 100 of FIG. 1 for supplying power to the implanted medical device 102. As shown in FIG. 2, the power source selection circuitry 126 of the external electronics 120 includes two inputs electrically coupled to the external battery 125 and building power source 112, respectively. Based on instructions from the control circuitry 122, the power source selection circuitry 126 outputs power from one of the external power sources to an input of the drive circuit 128. The drive circuit 128 amplifies the outputted power. The amplified power is then provided to the external coil 130. The external coil is coupled to additional circuitry such as one or more capacitors 135 that form a resonant circuit with the external coil. The capacitance may be between about 50 nF and 200 nF. The external coil 130 generates a magnetic field which inductively couples to the implanted coil 140 at the resonant frequency of the resonant circuits.

As described above, the external power source selection circuitry 126 may be controlled by the external control circuitry 122. For example, if the external control circuitry 122 determines that the external electronics 120 are not connected to a building power source 112, the external control circuitry 122 may instruct the external power source selection circuitry 126 to provide power to the external coil 130 from the external battery power source 125. For further example, if the external control circuitry 122 determines that the external electronics 120 are connected to a building power source 112, the external control circuitry 122 may instruct the external power source selection circuitry 126 to provide power to the external coil 130 from the building power source 112 instead.

The driver circuitry 128 may also be controlled by the external control circuitry 122. For example, the external control circuitry 122 may determine an appropriate setting (e.g., voltage, current, pulse width) at which the external coil 130 should be driven so as to inductively generate enough power at the implanted coil 140 that the implanted medical device 102 may be supplied with a sufficient amount of power. The power requirements of the implanted device will depend on the nature of the device and also may vary during operation of the device. For example, systems for use with a typical VAD may be arranged to transmit at least 5 watts, at least 10 watts, at least 15 watts, or at least 20 watts of continuous power to the implanted device 102.

At the implanted electronics 150, the rectifier circuitry 156 receives the AC power generated at the implanted coil 140, and rectifies the AC power to provide DC power. The rectifier circuitry 156 may include a diode bridge, synchronous rectifier or other components known in the art for AC-to-DC rectification. The DC output of the rectifier circuitry 156 is then input to the voltage regulator circuitry 158, where it is capped to a predefined voltage limit or threshold (e.g., 60V) by a voltage limiter, e.g., breakdown diodes. The voltage is further conditioned using a step-down DC to DC (DC-DC) converter 252, such as a buck switching controller, single-ended primary-inductor converter (SEPIC), or other components known in the art, to a voltage and current level required for powering the implanted medical device 102 (e.g., about 18V). Optionally, in some systems, the order of the rectifier circuitry and the voltage regulator may be reversed. For instance, the DC-DC converter may be replaced with a transformer used to convert the voltage level of the AC power, and the converted AC power may then be converted to DC power by the rectifier circuitry. The output of the voltage regulator circuitry 158 is provided to one of the inputs of the implanted power source selection circuitry 159. A second input of the implanted power source selection circuitry 159 is electrically coupled to the implanted battery 155. In the example of FIG. 2, the implanted battery 155 outputs a direct current that is coupled to an input of a DC-DC step-up or boost converter 254. The step-up converter 254 conditions the voltage and current level of the power output by the implanted battery 155 to a level required for powering the implanted medical device 102. For example, the step-up converter 254 may raise the voltage of the power output by the implanted battery 155 from about 12V to about 18V. The implanted power source selection circuitry 159 includes an output electrically coupled to the implanted medical device 102.

The implanted power source selection circuitry 159 is configured to switch between providing power to the implanted medical device 102 from one of an implanted battery 155 and the implanted coil 140. In similar fashion to switching regulation of the external circuitry 120, such internal switching may be determined based on inputs provided to the implanted control circuitry 152. Inputs to the implanted control circuitry 152 may also indicate an amount of voltage received at the implanted coil 140, and a temperature of the implanted electronics 150. For instance, if the implanted control circuitry 152 determines that not enough energy is received at the implanted coil 140, or that the temperature of one or more internal components is too high to safely operate, then the implanted control circuitry 152 may instruct the implanted power source selection circuitry 159 to supply power to the implanted medical device 102 from the implanted battery 155.

In addition to the circuitry for supplying power to the implanted medical device, the implanted electronics 150 also includes charging circuitry 256 for charging the implanted battery 155 using the generated wireless energy. The charging circuitry may be arranged so as to permit charging the implanted battery 155 even while wireless energy is supplied to the implanted medical device 102. The charging circuitry 256 may include one or more switches controlled by the implanted control circuitry 152.

In some examples, power provided to the implanted battery 155 may be controlled so as to avoid constant discharging and recharging of the implanted battery, (commonly referred to as "micro disconnects") which affect the battery life of TET powered VAD systems, for instance due to fluctuations in power demands from the implanted medical device 102. For example, commonly owned U.S. Pat. No. 8,608,635, the disclosure of which is hereby incorporated herein in its entirety, describes a TET system that dynamically adjusts the energy emitted by a transmitting coil based on power demands of an implanted VAD.

Figure 3:
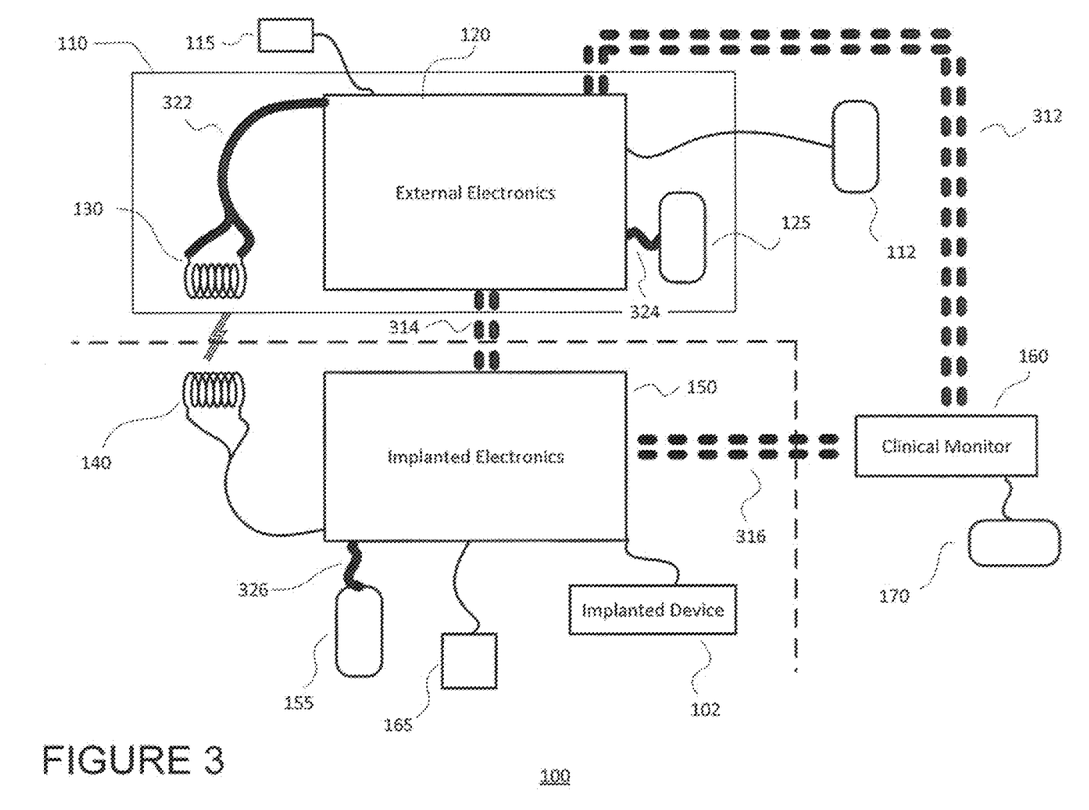
FIG. 3 is a schematic diagram of the communication system circuitry for the TET system of FIG. 1 in accordance with an aspect of the disclosure.

FIG. 3 schematically illustrates communication circuitry for enabling communication among the electronic components of the TET system 100. Each of the dotted lines 312, 314 and 316 represents a wireless communication channel between two of the components. Each of the solid lines 322, 324 and 326 represents a wired communication channel.

Beginning with the external electronics 120, the external electronics are communicatively coupled to each of the external coil 130 (via channel 322), external battery 125 (via channel 324), clinical monitor 160 (via channel 312), and implanted electronics 150 (via channel 314). The external electronics 120 may be wired to those components with which it shares a housing (e.g., in the present example, the external battery 125, housed together in module 110), and are wirelessly coupled to the separately housed components (e.g., in the present example, the separately housed clinical monitor 160). Communication between the external electronics 120 and any implanted component (e.g., the implanted electronics 150) is wireless.

In the example of FIG. 3, the sensors 115 associated with the external electronics are configured to measure each of the supply voltage and supply current for the connected power sources, including the wall power source 112 and the external battery power source 125. Additional sensors are configured to measure an amount of current supplied to the external power source selection circuitry (126 in FIGS. 1 and 2), as well as the temperature of the external coil 130 and associated electronics. In addition to these sensed values, the external electronics 120 may receive information signals from the implanted electronics 150 indicating other values associated with the TET system 100, such as the voltage and current at a load of the implanted coil 140, the voltage at the implanted rectifier circuitry 156, etc.

Beyond accumulating data from communicatively coupled components and sensors 115/165, the external electronics 120 may also share gathered data with other components of the TET system 100, such as with the clinical monitor 160 and implanted electronics 150. For example, the external electronics 120 may transmit all received and measured values to the clinical monitor 160 for further monitoring, logging, processing and/or analysis. Communication to the clinical monitor may be intermittent.

The implanted electronics 150 are responsible for gathering measured sensor values and data of the implanted components of the TET system 100. For instance, the implanted electronics 150 may receive information regarding the voltage and current at a load of the implanted coil 140. As described above, this data may be relayed to the external electronics 150 and/or clinical monitor 160 to further coordinate control and optimize efficiency between the transmitter (external) and receiver (implanted) sides of the system 100.

The external electronics 120, implanted electronics 150, and clinical monitor 160 may all communicate by radio frequency telemetry modules having RF transmitters and/or receivers, such as those modules described in commonly owned U.S. Pat. No. 8,608,635. For example, the external electronics may communicate with the clinical monitor (via channel 312) using a medical Bluetooth communication channel. The implanted electronics may communicate with the external electronics (via channel 314) and clinical monitor (via channel 316) using a medical implant communication service (MICS).

Figure 4:
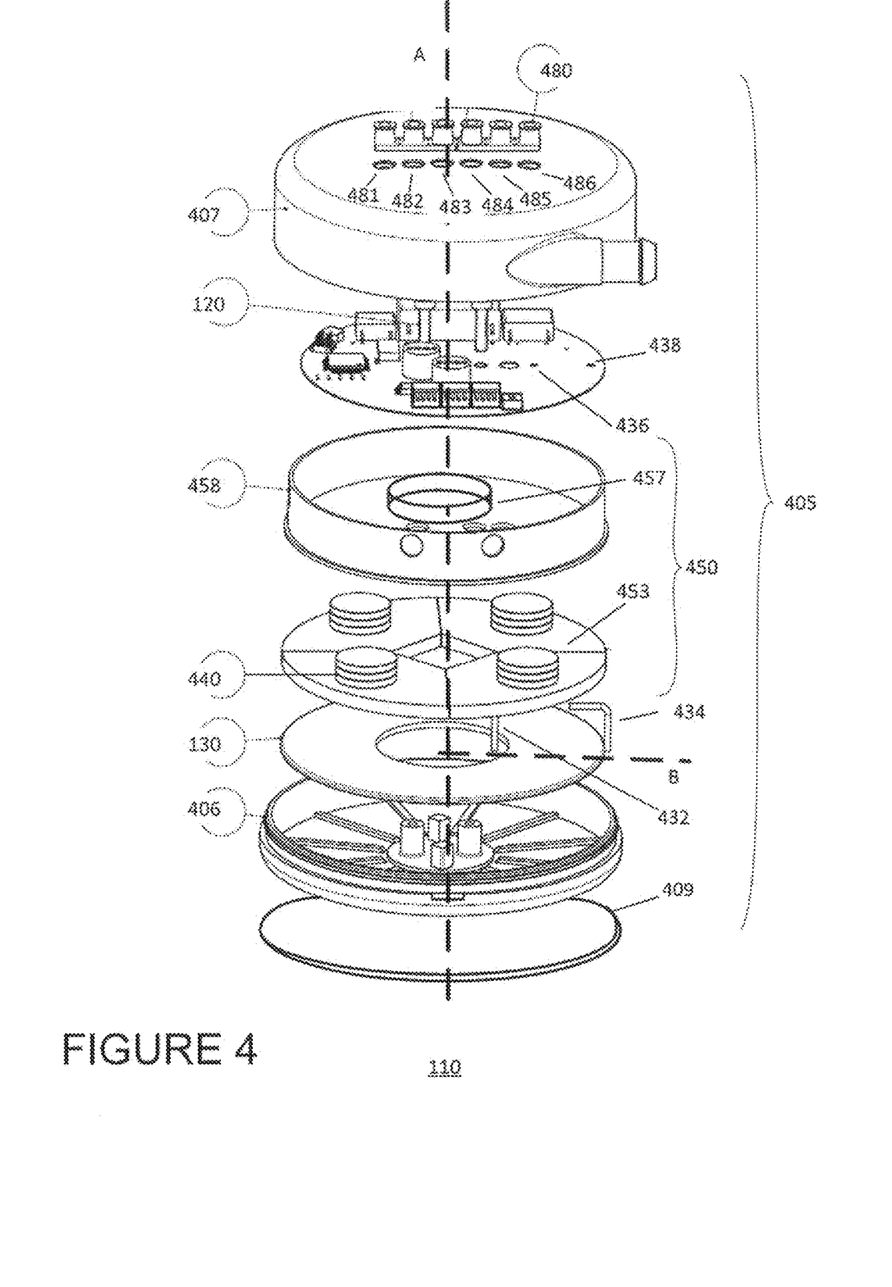
FIG. 4 is an exploded view of an external module of the TET system of FIG. 1 in accordance with an aspect of the disclosure.

One configuration of an external module 110 such as the module is depicted in FIGS. 4 and 5A-5C. FIG. 4 illustrates an exploded view of the external module 110. The external module 110 contains each of the external electronics 120 and a primary coil (the external coil 130) disposed entirely within a carrying system or housing 405. Efficiency of the external module is improved by integrating the power electronics and primary coil within a common housing. In TET systems having a separately housed primary coil and drive electronics, the distance between the coil and drive electronics (often 1 meter) can result in cable losses and overall weakness in the system. Co-locating the drive electronics and primary coil eliminates such cable losses, and enables a high Q and higher efficiency to be achieved.

In the example of FIG. 4, the housing 405 is made of a durable non-conductive material, such as a plastic. The housing includes each of an "outward-facing" cap 407 which faces away from the patient 104 and an "inward-facing" base 406 which faces towards the patient 104 when the module 110 is in use. The cap 407 and base 406 may fasten to one another by any suitable fastening modality as e.g., press fitting, spin welding, ultrasonic welding, adhesive, etc. In the example of FIG. 4, the module 110 is circular, although modules may take a different shape such as, e.g., square, oblong, etc. A thermal isolation layer 409 is integrated into the base 406 of the housing 405, or added as an additional layer on the surface of the inward facing side of the housing 405 to provide an additional thermal barrier between the primary coil and the patient's skin. The thermal isolation may be made of a polymer material (e.g., silicone), and may provide a breathable surface for the skin pores of the patient.

The external electronics 120 are arranged on a printed circuit board 420 (PCB) disposed near the "outward-facing" end of the module (e.g., within the cap 407) and extending transverse or perpendicular to a primary axis A of the module 110. The primary axis A extends in the outward direction, i.e., from the center of the base 406 to the center of the cap 407. The primary coil 430 is disposed near the opposite "inward-facing" end of the module (e.g., within the base 406). Such an arrangement ensures that the electronic components of the module do not interfere with the inductive coupling between the external and implanted coils 130 and 140 of the TET system 100.

Figure 5A:
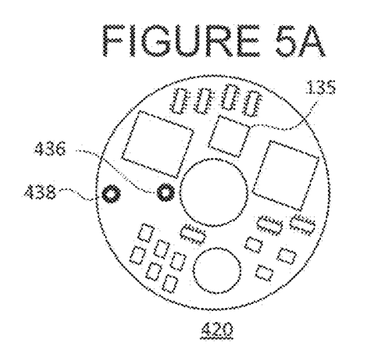
FIGS. 5A-5C. are top-down views of a printed circuit board, a shielding element, and an external wire coil included in the external module of FIG. 4 in accordance with an aspect of the disclosure.

The PCB 420 may be shaped to fit the housing 405 of the module 110. In the example of the circular module 110, the PCB 420 may be circular or annular in shape. FIG. 5A depicts a top down view of an annular shaped PCB 420 with a gap having a diameter between about 20 mm and about 35 mm in the center of the PCB 420, which lies on the primary axis A. The electronic circuit components, which may include one or more capacitors 135 and other components coupled to the external coil 130 to form a resonant circuit, are arranged around the gap. The gap in the center of the PCB 420 permits or at least simplifies connection of the electronic circuit components to the primary coil 130, although the gap may be omitted, such as from a circular PCB, and the primary coil 130 may be connected via a different path. Also, as described in greater detail below, the PCB 420 includes connection points 436 and 438 to facilitate connecting the primary coil 130 to the other electronic circuit components.

The housing 405 of the module 110 may be wide enough to contain a primary coil 130 with a diameter 70 mm or greater. For instance, the housing of FIG. 4 has an outer diameter of about 90 mm or greater. As such, the PCB 420 may be wide enough to fit inside the housing 405 without having to stack the capacitors physically above, or below, other components disposed on the PCB. As shown in FIG. 5A, the capacitors 135 may be disposed alongside the other circuitry on the PCB. In turn, the housing of FIG. 4 may be made thinner (i.e., along the primary axis), relative to a smaller diameter housing of similar design. In the example of FIG. 4, the housing 405 may have a thickness (at the primary axis A) of between about 10 mm and 20 mm (e.g., 15 mm).

The primary coil 430 is a substantially planar coil comprised of a single continuous conductor wire (e.g., Litz wire) wrapped in a planar spiral pattern around the primary axis A. As used in the present disclosure, the term "spiral" should be understood to include both curves that begin at the primary axis and wrap around the axis, as well as curves that wrap around the axis beginning at a location radially apart from the axis, thereby leaving a gap or opening at the center of the coil. The coil 130 may be wrapped anywhere between 5 and 15 turns. Based on the given value ranges, and based the formula for calculating air-core inductors $L=(d^2*n^2)/(18*d+40*l)$ (where d is the coil diameter, l is the coil length, and n is the number of turns in the coil), the coil 130 may have an inductance anywhere between 15 μH and 25 μH.

Figure 5B:
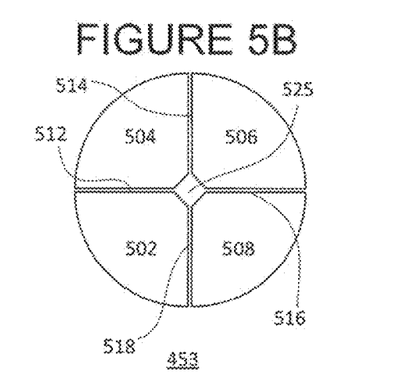
Figure 5C:
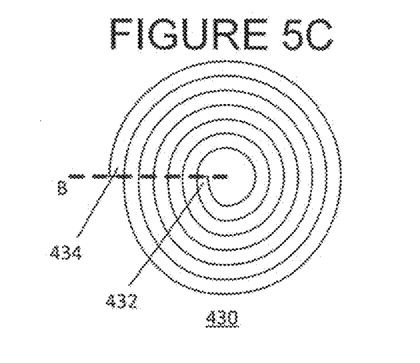

FIG. 5C depicts a top-down view of the primary coil 430. The conductor wire of the primary coil has an inner end 432 and an outer end 434. In the example of FIG. 5C, each of the wire ends 432 and 434 is disposed substantially at a common radial axis B extending radially from the primary axis A. As shown in FIG. 4, each of the wire ends 432 and 434 may curl upward and away from the plane of the coil 430 and towards the PCB 420. Each wire end may be soldered or otherwise connected to the respective connection points 436 and 438 on the PCB 420.

In order to shield the electronics of the PCB 420 from the magnetic field generated by the primary coil 130, the module 110 includes a shield 450 disposed between the PCB 420 and the primary coil 130. The shield 450 includes an annular disc 453 centered at and extending transverse to the primary axis A, and pair of concentric rings 457 and 458 defining a wall having a surface of revolution about the primary axis A and extending parallel to the primary axis A in the outward direction from the inner edge and outer edges of the annular disc 453, respectively.

The rings 457 and 458 may extend along the primary axis A for a length equal or greater than the height of the PCB 420 electronics such that the electronics (including the capacitors) are completely disposed within the semi-toroidal cavity formed by the shield 450.

Both the disc 453 and rings 457 and 458 are composed of a ferromagnetic or ferrimagnetic material (e.g., a ferrite) having an electrical conductivity less than about $\_0.3\times10^6\sigma$ and a relative permeability of between about 2000 and about 12000. The disc 453 may be a rigid plate having a thickness (in the primary axis A direction) between about 1 mm and about 2 mm, and the rings 457/458 may be made of a flexible foil, each having a thickness (in the radial axis B direction) between about 0.5 mm and about 1 mm. Other example modules (e.g., a module having a circular PCB with no gap) may include a circular shield with no hole in the center and a single ring extending from the outer edge of the disc. In such an example, the PCB 420 electronics (including the capacitors) may be completely disposed within the regular shaped cavity formed by the shield 450. Yet further examples may include a shield that is made from a single piece of ferromagnetic or ferrimagnetic material and molded into a regular or semi-toroidal shape, depending on whether the module 110 includes a circular or annular PCB, respectively.

The shield 450 is disposed between the PCB 420 and the external coil 430 along the primary axis A. The disc 453 of the shield 450 redirects or focuses the magnetic field emitted from primary coil towards the secondary coil 140 implanted within the patient. This focusing increases the coupling coefficient of the TET system 100, and further protects the electronics of the PCB 420 from unwanted inductive coupling. The inner and outer rings 457 and 458 provide further protection, effectively guiding the magnetic field around (instead of through) the annular PCB 420.

The disc 453 may be made up of multiple segments or sections. FIG. 5B illustrates a top-down view of a disc 453 having quarter segments 502-508, although other discs may have a different number of segments (e.g., 2-8 segments). Each segment has a radius of between about 20 mm and about 35 mm. Gaps 512-518 are present between edges of mutually adjacent segments. The gaps 512-518 may be formed by cutting the disc during assembly, and may extend substantially radially from the primary axis A at the center of the disc 453. The gaps range from 0 mm to 0.5 mm. In the example of FIG. 5B, each segment is about 1.5 mm thick (i.e., along the primary axis A). Sectioning the disc 453 in the above manner is believed to improve efficiency of the TET system. At the center of the disc 453 is an internal hole 525. In the example of FIG. 5B, the internal hole 525 is square, as such shape is believed to achieve an optimal scatter field characteristic for coupling the primary and secondary coils 130 and 140. The size of the internal hole 525 may range from 20 mm to 35 mm, and in some examples may be shaped differently (e.g., circular, rectangular, triangular, etc.).

Each of the rings 457 and 458 may include a small slit (not shown) to permit passage of the primary coil wire through the rings in order to connect the conductor wire ends 432 and 434 of the primary coil 430 to the respective connection points 436 and 438 of the PCB 420. The inner wire end 432 at the inner perimeter of the primary coil 130 may pass through the slit of the inner ring 457 to the inner connection point 436, and the outer wire end 434 at the outer perimeter of the primary coil 130 may pass through the slit of the outer ring 458 to the outer connection point 438. The slits may be radially aligned with one another such that the wire ends connect to the PCB 420 at substantially the same area of the PCB 420. In an alternative example, the rings 457 and 458 may not include slits and each wire end 432 and 434 may curl over and around a respective ring on order to connect to the connection points 436 and 438 of the PCB 420.

Also shown in FIG. 4 are spacers 440, disposed between the disc 453 and the PCB 420. The spacers 440 provide sufficient distance between the PCB 420 and the disc 453 in order to prevent possible shorting due to the conductivity of the disc 453. The spacers are preferably made from a non-conductive, non-magnetic, material such as plastic, and may have a thickness between about 1 millimeter and about 10 millimeters (e.g., about 6 millimeters thick). The example module of FIG. 4 depicts four spacers, each spacer displaced over a respective segment 502-508 of the disc 453. Other examples may include more or fewer spacers (e.g., 2 spacers, 8 spacers, etc.).

Also shown in FIG. 4 at the outward facing side of the cap 407 is a visual indicator 480 including a plurality of light emitting diodes (LEDs) 481-486. As described below, the LEDs 481-486 are configured to indicate the position of the external primary coil 130 relative to an implanted secondary coil 140 and to further indicate a direction and/or distance that the implanted coil 140 must be moved in order to better align with the implanted coil 140. The example module of FIG. 4 depicts a row of six LEDs, but other examples may other display technologies known in the art but also include more or fewer lights (e.g., 5 LEDs, 8 LEDs, etc.), and the lights may be arranged in other configurations (e.g., a grid, a circle, etc.).

Figure 6:
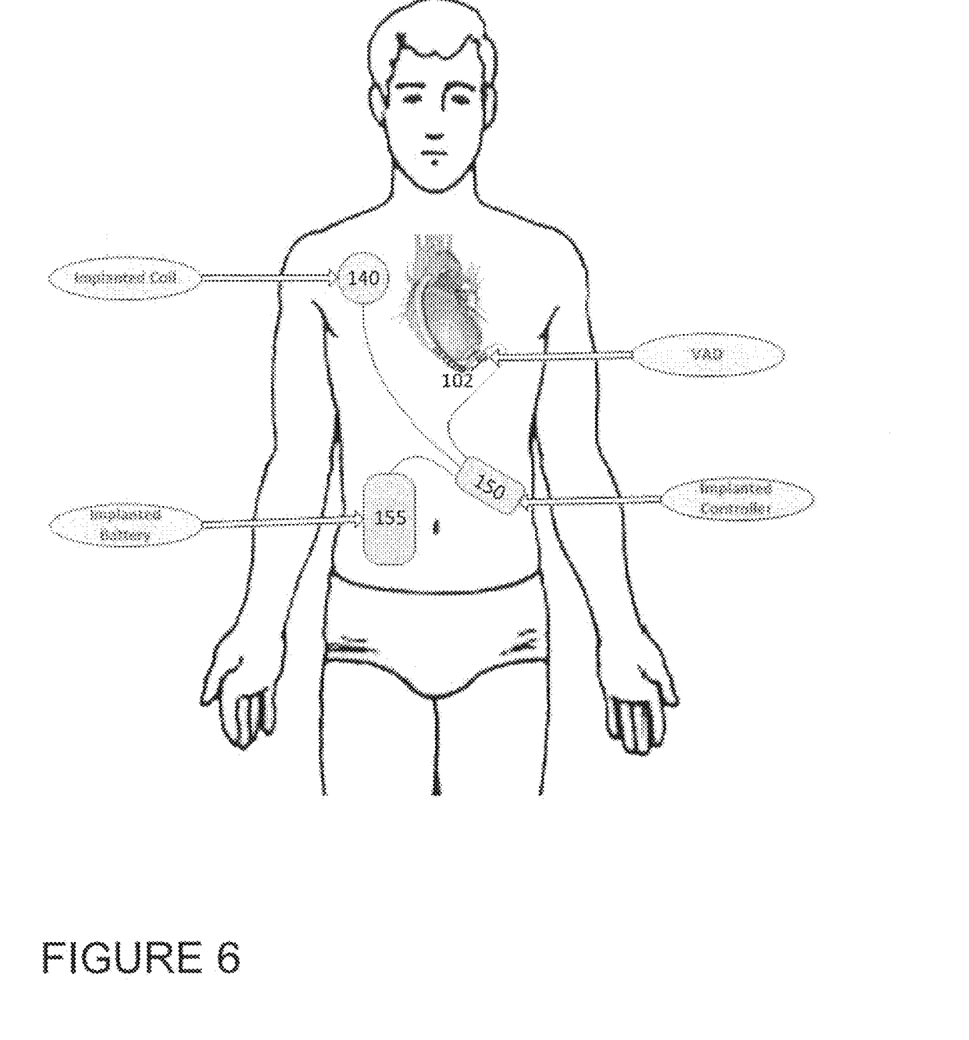
FIG. 6 is a schematic diagram of the implanted components of the TET system of FIG. 1 in accordance with an aspect of the disclosure.

Turning now to the implanted components of the TET system 100, FIG. 6 illustrates a schematic view of an example arrangement of the components implanted within the patient 140. As shown in FIG. 6, each of the implanted coil 140, the implanted battery 155, the implanted medical device 102, and the implanted electronics 150 is disposed in a separate housing and dispersed throughout the patient's body in order to accommodate the anatomy of the patient. Each of the implanted coil 140, battery 155 and medical device 102 is electrically coupled to the implanted electronics 150 via a separate electrical power cable.

As discussed above, the secondary coil 140 is inductively coupleable to a primary coil 130. Positioning of the secondary coil 140 within the patient may be done in such a manner that makes mounting the external module 110 in proximity to the secondary coil 140 easy for the patient. For instance, the secondary coil 140 may be positioned close to the skin of the patient. Moreover, the secondary coil 140 may be positioned close to a relatively flat part of the patient's body to make mounting the external module 110 easier. In the example of FIG. 6, the secondary coil 140 is positioned close to the front of the patient's chest, such that mounting the external module 110 to the patient's chest is easy and puts the external module 110 in close proximity to the secondary coil 140.

Figure 7:
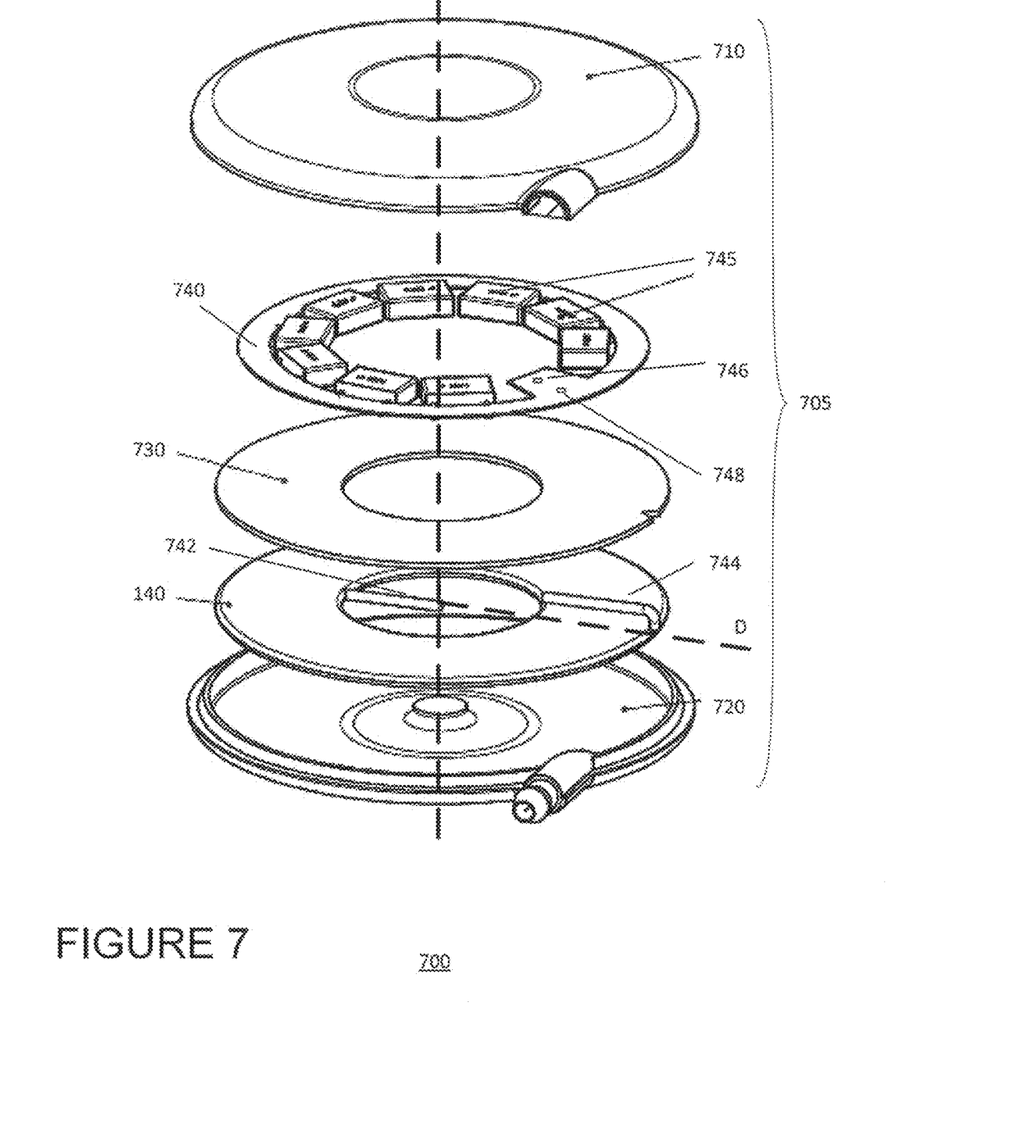
FIG. 7 is an exploded view of an implanted coil module of the TET system of FIG. 1 in accordance with an aspect of the disclosure.

FIG. 7 illustrates an exploded view of an implanted coil module 700 containing the secondary coil 140. As shown in FIG. 7, the secondary coil 140 is disposed within a housing 705 of the module 700 having a cap 710 and base 720 that fit together. Fitting the cap 710 and base 720 together may be accomplished in any suitable manner known in the art, such as those described above in connection with the external module 110, and may be the same or different as fitting the cap 408 and base 406 of the external module 110. The housing 705 may be made of a biocompatible material with a dissipation factor suitable to avoid overheating the module 700 or surrounding tissue. Preferably, the housing does not increase more than about two degrees (° C.) due to heat generated from inductive charging between the primary coil 130 and secondary coil 140.

Each of a circuit board 740 holding one or more capacitors 745 (e.g., collectively acting as a high-voltage bulk capacitor), a shield 730, and a secondary wire coil 140 are disposed entirely within the housing 705, and extend transverse or perpendicular to a secondary axis C of the module 700. The secondary axis C extends in the inward direction, i.e., from the center of the base 710 to the center of the cap 720. The secondary coil 140 is preferably disposed proximate the base 720 of the housing 705, which is adapted to be implanted closer to the skin of the patient (and therefore closer to the external module 110), and the board 740 with the capacitors 745 is preferably disposed proximate the cap 710 of the housing 705 farther from the patient's skin. Additionally, the cap 710 and/or base 720 of the housing 705 may include one or more visually perceptible indicia to indicate or differentiate which side of the housing 705 is front facing (i.e., the secondary coil 140 being disposed at that side) and which side of the housing 705 is rear facing (i.e., opposite the front facing side). The indicia aid implantation of the secondary coil module 800 in its proper orientation to maximize the coupling coefficient between the external and secondary coils 130 and 140.

Figure 8A:
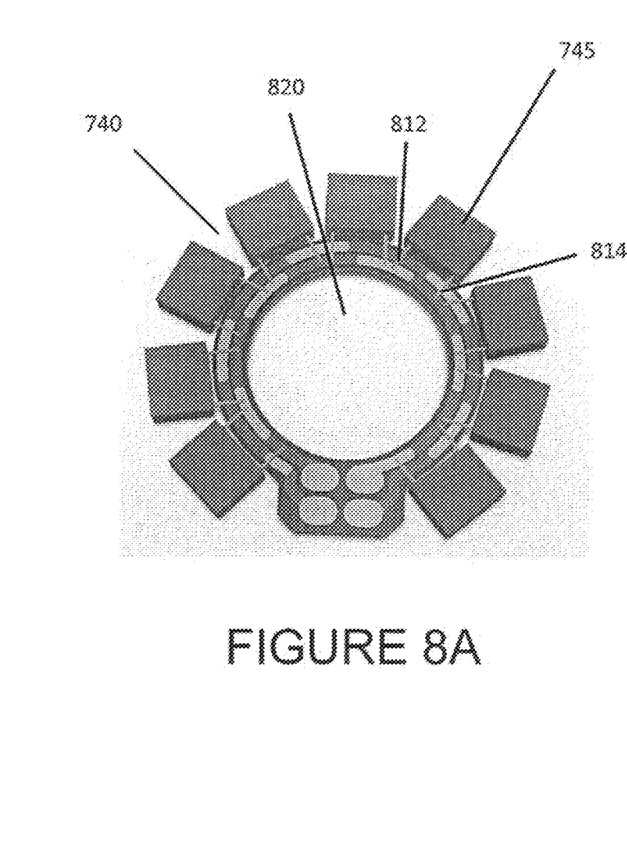
FIGS. 8A and 8B are top down views of implementations of a circuit board included in the implanted coil module of FIG. 7 in accordance with aspects of the disclosure.
Figure 8B:
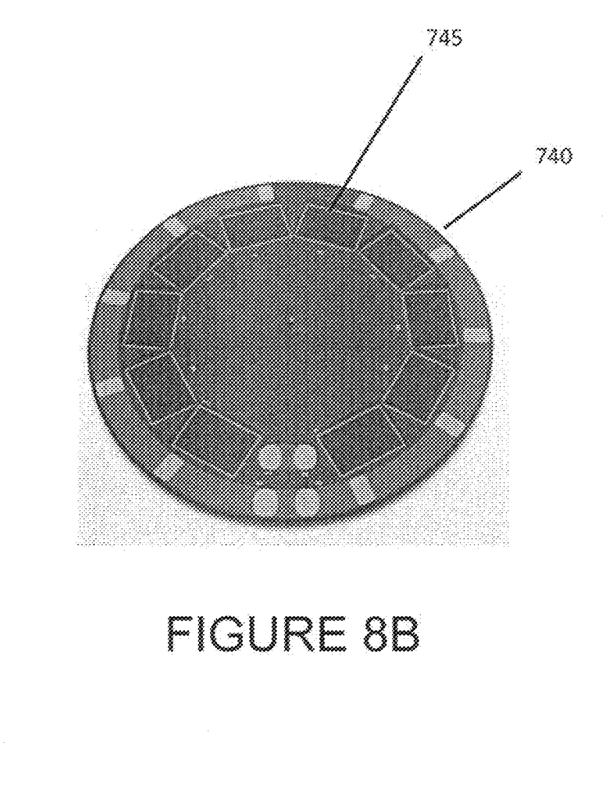

The capacitors 745 are evenly distributed around the circuit board 740 in order to distribute heat losses over a larger, more unified area. FIGS. 8A and 8B illustrate alternative arrangements of the circuit board and capacitors. In FIG. 8A, the capacitors 745 are positioned at the outer perimeter 810 of a ring shaped circuit board 740 having an opening 820 at the center. Each of the capacitors is electrically connected to the ring via pins (e.g., 812, 814). In FIG.

8B, the capacitors 745 are positioned in a circular pattern on a solid (no opening in the center) circuit board 740. Both arrangements permit for heat losses to be evenly distributed due to the even distribution of the capacitors.

The shield 730 is disposed between the board 740 and the secondary coil 140. As with the shielding 450 of the external module 110, the shield 730 is beneficial both for shielding the board 740 from inductive coupling, as well as improving the focusing of the magnetic field generated at the primary coil 130, thereby increasing the coupling coefficient between the primary and secondary coils 130 and 140.

In the example of FIG. 7, the implanted coil 140 is a substantially planar coil comprised of a single continuous conductor wire (e.g., Litz wire) wrapped in a spiral pattern around the secondary axis C. The coil 140 may be wrapped anywhere between 5 and 15 turns, and may have a diameter substantially equal to the diameter of the primary coil 130, for example about 80 mm or more. The conductor wire may be electrically coupled to the capacitors 745 at each of an inner wire end 742 and an outer wire end 744. In order to connect the wire ends 742 and 744 to the capacitors 745, the ends may be curled upward and away from the plane of the coil 740 (which is transverse to the secondary axis C) and generally axially towards the board 740. Electrical connection between the wire ends 742 and 744 and the capacitors 745 may be established by soldering each wire end to a respective connection point 746 and 748 on the board 740 holding the capacitors 745. As shown in FIG. 7, each of the wire ends 742 and 744 and connection points 746 and 748 may be disposed substantially at a common axis D extending radially from the secondary axis C.

The board 740 may be annular shaped having a circular inner hole between about 30 mm and about 70 mm in diameter (e.g., 17.5 mm), and a thickness (in the secondary axis C direction) of about 1 mm. As described above, the board 740 may include one or more capacitors 745 that are coupled to the secondary coil 140, and having a capacitance of between about 100 nF and 150 nF. Together, the secondary coil 140 and capacitors 745 form a resonant circuit. The resonant circuit has a pair of load terminals (which may be the connection points 846 and 848) disposed within the housing 705. In some examples, the board may optionally include additional circuitry for adjusting the resonant frequency of the resonant circuit, for instance through selective coupling of the capacitors, and may also optionally include one or more temperature sensors for monitoring the temperature of the implanted coil module 700. The board 740 of FIG. 7 is shown holding 9 capacitors in a ring, but other example boards, such as those of similar shape and size, may fit more (e.g., 10) or fewer (e.g., 2 or 3) capacitors, and the capacitors may be arranged differently (e.g., in a grid).

Additionally shown in FIG. 7 is a port 715 built into both the cap 710 and base 720 of the housing 705. The port is adapted to permit one or more power cables or wires (not shown) to pass therethrough such that the cables or wires electrically connect the components disposed within the housing 705 to the implanted electronics 150. For instance, a cable having conductors may pass through the port 715 in order to electrically connect the load terminals disposed in the housing 705 to the implanted electronics 150. It is preferable to include the capacitors 755 on the implanted coil 140 side of the cable (i.e., in the implanted coil module 700) to reduce the distance from the implanted coil 140 and the load terminals. This in turn minimizes any power losses over the cable. Returning to FIG. 6, the implanted electronics 150 are electrically coupled to, but housed separately from, the implanted coil 140. The implanted electronics 150 may separated between two or more circuit boards, such as a voltage rectifier board and control board. The voltage rectifier board would include the voltage rectifier circuit 156 described above in connection with FIGS. 1 and 2, which rectifies AC power generated at the implanted coil into DC power. The voltage rectifier board also would include the voltage regulator circuitry 158 described above, which conditions the voltage supplied to the implanted medical device 102 to a required level, as well as the implanted power source selection circuitry 159 for switching between providing power to the implanted medical device 102 from the implanted battery 155 and the implanted coil 140.

The control board would include circuitry, such as a MOSFET inverter, responsible for driving the implanted medical device 102, as well as the control circuitry 152 responsible for instructing a power source selection of the implanted power source selection circuitry 159. The control circuitry 152 may determine proper operation parameters of the implanted coil 140 (e.g., a resonant frequency), and whether to power the implanted medical device 102 using energy from the implanted coil 140, from the implanted battery 155, or both. The control board may additionally collect and communicate various data about the TET system 100. For example, the control board may be configured to receive, interpret, store and/or relay information regarding the temperature of the power source selection circuitry 159. For further example, where the implanted medical device 102 is an implantable pump, such as the VAD of FIG. 7, the control board may be configured to handle information transmitted from sensors 165 at the pump, such as back-EMF exhibited by the pump, and electrical current at the pump's stators. Storage of such information may be done on a memory included on the control board, and the information may be communicated to other components of the TET system 100, such as the external electronics 120 and the clinical monitor 160, using the RF telemetry circuitry 154 discussed above.

In an alternative embodiment, the voltage rectifier board and control board may be housed separately. In such examples, the cable extending from the housing 705 of the implanted coil module 700 (described above in connection to FIG. 7) electrically connects to an input terminal of the rectifier housing, and from there connects to an input terminal of the rectifier circuitry 156. As such, the rectifier circuit is electrically coupled between the implanted coil 140 and the implanted medical device 102 such that only load current passing from the capacitors 845 passes along the conductors of the cable to the rectifier circuitry 156 to the implanted medical device 102. In other examples, the voltage rectifier board and control board may be housed together, with the cable extending from the housing 705 of the implanted coil 140 electrically connecting to an input terminal of the common housing.

The implanted battery 155 may be a cell lithium ion cell/battery housed within a titanium or medical grade plastic casing. In the case of powering a VAD, the battery may be configured to store charge between about 12 volts and 16.8 volts. As stated above, the implanted battery is coupled to the implanted medical device 102 in order to power the implanted medical device 102 in response based on a determination by the implanted control circuitry 152. The implanted battery 155 may also be electrically coupled to the implanted coil 140 through the voltage rectifier board of the implanted circuitry 150 in order to temporarily store power generated at the implanted coil 140 in excess of the power needed at the implanted medical device 102. That excess power may be used to charge the implanted battery 155 for later use in operating the implanted medical device 102.

In an alternative embodiment to the example arrangement of FIG. 6, the implanted coil may be disposed in a housing that is mounted to the implanted medical device. For instance, FIG. 9 illustrates an perspective view of the implanted medical device 102 (which is in this example a ventricular assist device, or VAD, for assisting cardiac function of the patient) having an implanted coil housing 905 mounted to a flat end 902 of the VAD 102. The flat end 902 of the VAD 102 is preferably positioned facing away from the heart and towards the chest of the patient, such that the implanted coil is positioned close to the patient's skin. Further, the implanted coil housing 905 is preferably mounted such that the implanted coil 140 disposed therein faces towards the chest of the patient so that the coil shield is positioned between the implanted coil and the VAD 102. This permits the implanted coil 140 to be positioned proximate to an external module 110 mounted to the chest of the patient, maximizing coupling between the external and implanted coils, while further shielding the magnetic components and conductive surfaces of the VAD from the electromagnetic TET field. The alternative arrangement of FIG. 9 is also advantageous for providing a heat sink for the VAD. The implanted electronics are also mounted to VAD 102. This makes implantation of the VAD and TET system significantly simpler, since there are no additional device pockets and no cabling between the implanted coil housing 905, implanted electronics 907 and VAD 102.

The TET system collectively described above may include additional features further improving upon several aspects of the system's operation. One such feature is the implementation of normal, start-up, and safe mode routines for operation, as well as testing routines for determining In which mode to operate. The testing routines provide for the TET system 100 to drive the external coil 130 using different amounts of current. Under normal mode operation, when the external components of the TET system 100 are in proper communication with the implanted components, the drive circuitry 128 applies a power level alternating potential (e.g., a maximum amount of current) to drive the external coil 130. As described above, under normal operation, the TET system may generate at least 5 watts, at least 10 watts, at least 15 watts, or at least 20 watts of continuous power. This power may be used to operate all power demands of the implanted medical device, RF telemetry needs, primary and back-up electronic system requirements, and further to power to recharge the implanted battery. If, however, one or more of the external components, such as the wireless energy transfer coils or RF telemetry coils, are not in properly coupled with one or more corresponding implanted components, less current may be applied to drive the external coil 130. The amount of reduction of the current may be based on the particular component or components that are not properly coupled.

The start-up routine may determine between operating the TET system 100 in one of the start-up and normal modes, and may be controlled by the external control circuitry 122. In the start-up routine, the TET system 100 may begin in start-up mode by applying a test-level alternating potential to drive the external coil 130 in order to test the degree of coupling between the external coil 130 and the implanted coil 140. The test-level alternating potential generates enough power to sense an implanted system or coil, but not enough power to operate the implanted device. For example, the test-level alternating potential may generate about 250 mW or less. The sensors 115 of the external control circuitry 122 may include a coupling detection circuit operative to detect the degree of inductive coupling between the external coil 130 and the implanted coil 140. This detection may be performed at least in part using a current monitor to measure the current flow in the external coil 130. Information regarding the detected coupling may then provided from the coupling detection circuit to the external control circuitry 122. The external control circuitry 122 may then determine, based on the provided coupling information, whether to continue in start-up mode or transition to normal mode.

If the external control circuitry 122 is in normal mode and does not receive an indication (or otherwise determines) that the external and implanted coils 130 and 140 are properly coupled, the external control circuitry 122 may instruct the drive circuitry 128 to cease application of the power-level alternating potential to drive the external coil 130, and may further transition to start-up mode and apply the test-level alternating potential to the external coil 130. The test-level alternating potential may be applied intermittently to determine whether the external and implanted coils 130 and 140 are properly or sufficiently coupled. The test-level alternating potential may provide sufficient current to determine the presence of inductive coupling without generating a magnetic field strong enough to harm the patient (such as overheating the skin or tissue of the patient) despite the lack of inductive coupling between the external and implanted coils 130 and 140. Additionally, the test-level alternating potential avoids unnecessary expenditure of power, while still enabling the external control circuitry 122 to continue monitoring and evaluating the coupling between the coils 130 and 140.

In the safe-mode routine, the level of wireless power transmitted may be determined based on whether the RF telemetry circuits of the external and implanted electronics 124 and 154 are properly communicating with one another. For example, if the external control circuitry 122 determines that a receiver of the external RF telemetry circuitry 124 is not receiving RF telemetry signals from a transmitter of the implanted RF telemetry circuitry 154, then the external control circuitry 122 may instruct the drive circuitry 128 to apply a relatively low power-level alternating potential to the external coil 130. In other words, the drive circuitry 128 would apply less current (a shorter pulse width) to the external coil 130 in the safe mode as compared to a normal mode of operation. The low power-level alternating potential would be strong enough to drive the external coil 130 to generate enough power to operate the implanted medical device 102. For example, with respect to a VAD, the power needs of the VAD may be defined by the blood flow needs of the patient (which in turn may be programmed by clinical staff). Such power needs can range from about 2 watts to about 5 watts.

The external control circuitry may be configured to implement both start-up and safe mode routines. Under such conditions, the drive circuit 128 may be operative to apply the low power-level alternating potential to the external coil 130 only if the coupling detection circuitry determines that the coils are properly coupled, and the external control circuitry determines that the external RF telemetry circuitry 124 is not receiving RF telemetry signal from the implanted electronics.

Another feature of the TET system is an alignment protocol for aiding a user in properly aligning the external and implanted coils in order to maximize efficiency of energy transfer therebetween.

The external control circuitry 122 may determine the then-present degree of coupling between the external and implanted coils 130 and 140 based on received information from the sensors 115. The information may be received in the form of input signals. One such signal may be provided by a voltage or current monitor coupled to the external coil 130, and may indicate an amount of voltage and/or amount of current at the external coil 130. Another such signal may be provided by the external RF telemetry circuitry 124 and may be indicative of power transfer (e.g., a coupling coefficient, or a current efficiency) between the coils. The telemetry signal may be received from the implanted RF telemetry circuitry 154, which itself is coupled to an implanted sensor 165 that measures current in the implanted coil 140.

The external control circuitry 122 alerts the patient as to the degree of coupling between the external and implanted coils 130 and 140.

Such alerts may be conveyed visually, such as by activating a human perceptible signal, such as with visual or aural indicator. In the example of the visual indicator, the indicator may include a number of lights or LEDs (e.g., the LEDs 481-486 on the outward facing cap 407 of the external module 420 of FIG. 4). For example, the number of lights activated may indicate the degree of coupling. The number of lights activated for any given degree of coupling may be preconfigured, for instance such that the greater the degree of coupling, the more (or alternatively, the fewer) lights that are activated.

The above disclosure generally describes a TET system for use in a user having an implanted VAD. Nonetheless, the disclosure is similarly applicable to any system having a transcutaneous stage of wireless power delivery. As such, the disclosure is similarly applicable for driving any power-consuming device implanted in any human or other animal (e.g., hearing aids, pacemakers, artificial hearts, etc.).

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A transcutaneous energy transfer system comprising:
a plurality of implanted electronics including an internal telemetry transmitter, an internal component comprising a power-consuming device and an internal coil electrically connected to the power-consuming device, the internal component being adapted for mounting within the body of an animal;
an external module housing a plurality of external electronics for communicating with the plurality of implanted electronics, the plurality of external electronics including an external telemetry receiver in communication with the internal telemetry transmitter;
an external coil adapted for mounting outside of the body;
a current monitor operative to measure current flow in the external coil and to provide an indication of whether or not the external coil is electromagnetically coupled to the internal coil based on the measured current flow;
an external control circuit for determining whether the plurality of implanted electronics are communicating with the plurality of external electronics;
a drive circuit operative to apply a power-level alternating potential to the external coil responsive to an indication from a coupling detection circuit that the external coil is electromagnetically coupled to the internal coil, and to apply an initial test-level alternating potential that is less than the potential required to operate the device and less than the power-level alternating potential to the external coil when not applying the power-level alternating potential, an amount of the applied alternating potential varying according to whether the internal coil and the internal telemetry transmitter of the plurality of implanted electronics are communicating with the external coil and the external telemetry transmitter of the plurality of external electronics; and
a control circuit operative to control the drive circuit responsive to information from the external telemetry receiver.

2. A system as claimed in claim 1 wherein the drive circuit is operative to cease application of the power-level alternating potential to the external coil in response to an indication from the coupling detection circuit that the external coil is not electromagnetically coupled to the internal coil.

* * * * *